United States Patent [19]

Jones, Jr. et al.

[11] 4,092,304

[45] May 30, 1978

[54] 4-SUBSTITUTED ENKEPHALIN DERIVATIVES

[75] Inventors: David A. Jones, Jr., Evanston; James M. Schlatter, Glenview; Richard A. Mikulec, Chicago; Judith A. Reuter, Skokie, all of Ill.

[73] Assignee: G. D. Searle & Co., Chicago, Ill.

[21] Appl. No.: 712,460

[22] Filed: Aug. 9, 1976

[51] Int. Cl.$^2$ .................. C07C 103/52; A61K 37/00
[52] U.S. Cl. ........................... 260/112.5 R; 424/177
[58] Field of Search .................. 260/112.5 R; 424/177

[56] References Cited

U.S. PATENT DOCUMENTS 3,272,790  9/1966  Bernardi et al. .............. 260/122.5 R

OTHER PUBLICATIONS

Li, et al; Nature, 260, 1976, p. 624.
A. Waterfield, et al; Nature, 260, 1976, p. 625.
J. Hughes, et al; Nature, 258, 1975, pp. 577–579.
A. Day, et al; Chem. Abst., 85, 1976, 117055t.
W. Voelter, et al; Tet. Let. 25, 2119–2120, 1976.

Primary Examiner—Delbert R. Phillips

[57] ABSTRACT

Analogs of methionine$^5$-enkephalin and leucine$^5$-enkephalin wherein the L-phenylalanyl residue in position 4 has been substituted by various other amino acid residues are disclosed herein. These analogs exhibit agonist activity at opiate receptor sites and are thus useful as analgesics, non-addicting narcotic antagonists and antidiarrheal agents.

3 Claims, No Drawings

4-SUBSTITUTED ENKEPHALIN DERIVATIVES

BACKGROUND OF THE INVENTION

This invention relates to analogs of methionine[5]-enkephalin and leucine[5]-enkephalin wherein the L-phenylalanyl residue in position 4 has been substituted by various amino acid residues. Enkephalin, a naturally occurring pentapeptide, has been isolated and found to be a mixture of two pentapeptides which differ only in the fifth amino acid residue. Leucine[5]-enkephalin is thus represented by the following structural formula

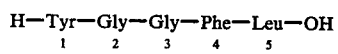

and methionine[5]-enkephalin by the following formula

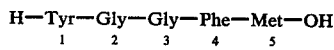

wherein the Tyr, Phe, Met and Leu residues are all of the L-stereochemical configuration.

SUMMARY OF THE INVENTION

The present invention is concerned with novel analogs of methionine[5]-enkephalin and leucine[5]-enkephalin. More particularly, this invention is concerned with compounds of the formula

wherein Y represents Leu or Met; W represents Trp, Tyr, Alkyl-Phe, hexahydro-Phe, β-thienyl-Ala, or Gly, with the condition that when W is Gly, Y cannot be Met; and the stereochemical configuration of each of the optically active amino acid residues may independently be D, L, or DL.

The alkyl group referred to above contains 1 to 8 carbon atoms and is exemplified by methyl, ethyl, propyl, butyl, pentyl, hexyl, heptyl, octyl and the corresponding branched-chain isomers thereof.

Abbreviations connote the amino acids defined in accordance with the nomenclature rules published by the IUPAC-IUB Commission on Biochemical Nomenclature in Biochem. J., 126, 773–780 (1972). The amino acids have the L-stereo-chemical configuration unless otherwise indicated.

The compounds of the present invention are represented in the following table. The W and Y substituents relate to Formula I, and the stereochemical configuration of each of the optically active amino acid residues may independently be D, L, or DL.

| W | Y | H-Tyr-Gly-Gly-W-Y-OH (I) |
|---|---|---|
| Trp | Leu | H-Tyr-Gly-Gly-Trp-Leu-OH |
|  | Met | H-Tyr-Gly-Gly-Trp-Met-OH |
| Tyr | Leu | H-Tyr-Gly-Gly-Tyr-Leu-OH |
|  | Met | H-Tyr-Gly-Gly-Tyr-Met-OH |
| alkyl-Phe | Leu | H-Tyr-Gly-Gly-alkyl-Phe-Leu-OH |
|  | Met | H-Tyr-Gly-Gly-alkyl-Phe-Met-OH |
| hexahydro-Phe | Leu | H-Tyr-Gly-Gly-hexahydro-Phe-Leu-OH |
|  | Met | H-Tyr-Gly-Gly-hexahydro-Phe-Met-OH |
| β-thienyl-Ala | Leu | H-Tyr-Gly-Gly-β-thienyl-Ala-Leu-OH |
|  | Met | H-Tyr-Gly-Gly-β-thienyl-Ala-Met-OH |
| Gly | Leu | H-Tyr-Gly-Gly-Gly-Leu-OH |

Preferred compounds of this invention are those of formula (I) wherein Y and W are defined as hereinbefore, and all the optically active amino acid residues are of the L stereochemical configuration.

Equivalent to the enformulated compounds for the purposes of this invention are solvates thereof in which biologically insignificant amounts of solvent are present.

Also equivalent to the compounds of formula (I) for the purposes of this invention are the pharmaceutically acceptable acid addition salts thereof. Such acid addition salts can be derived from a variety of inorganic and organic acids such as sulfuric, phosphoric, hydrochloric, hydrobromic, hydriodic, nitric, sulfamic, citric, lactic, pyruvic, oxalic, maleic, succinic, tartaric, cinnamic, acetic, trifluoroacetic, benzoic, salicylic, gluconic, ascorbic and related acids.

DETAILED DESCRIPTION OF THE INVENTION

The compounds of the present invention are useful in consequence of their valuable pharmacological properties. They are, for example, agonists at opiate receptor sites. Such agonists are useful as analgesics, narcotic antagonists and anti-diarrheal agents.

The assay utilized for detection of the agonist activity at opiate receptor sites is a modification of the technique described by Pert, Snowman and Snyder, In *Brian Research*, 70, 184 (1974).

Details of that assay are as follows: Guinea pigs weighing 600–700 grams are killed and the whole brains removed and homogenized in 0.32 M sucrose after removal of the cerebella. The homogenate is centrifuged at 1000 + g. for ten minutes, the pellet discarded, and the supernatant fraction centrifuged at 17,500 × g. for ten minutes. The pellet is osmotically shocked with ice-cold water and recentrifuged at 10,000 × g. for 10 minutes. The resultant supernatant, containing the membrane fraction used for the binding assay, is diluted with 0.05 Tris buffer (pH 7.4 at 25° C.) to a protein concentration of 2 mg/ml.

Aliquots of the final membrane suspension are incubated with varying concentrations of the test compound. Aliquots incubated with $10^{-6}$ M levorphanol are used to determine non-specific binding of the radioactive liquid. The assay is run at 4° C. and is initiated with the addition of 8mM $^3$H-naloxone (specific activity greater than 20 Ci/mmole). The reaction is terminated by rapid filtration of the incubation mixture on GF/B glass filter papers. The membranes trapped on the filter paper are washed twice with ice-cold Tris buffer. The amount of radioactive ligand bound is determined by liquid scintillation techniques. An $ID_{50}$ concentration of the $^3$H-naloxone binding is determined from log-probit curves of the percent inhibition of $^3$H-naloxone binding versus concentration of the test compound.

The in vitro assay described is widely known to correlate with relative agonist-antagonist properties in vivo; *Nature*, vol. 247, Jan. 11, 1974. When known agonists-antagonists such as morphine and methadone were tested by this assay, in the absence of sodium ion, they had $ID_{50}$ concentrations of $1.2 \times 10^{-8}$ and $2.4 \times 10^{-8}$ respectively.

It is also known that the receptor affinities in the ileum are similar in their binding characteristics with those of the brain. Lars Terenius, *Acta. Pharmacol. et Toxicol.*, 37, 211–221 (1975). Available evidence indicates that drugs which act on the ileum opiate receptors cause constipation, and are therefore useful as anti-diarrheal agents.

The compounds of formula (I) may be combined with various typical pharmaceutical carriers to provide compositions suitable for use as analgesics, as narcotic antagonists for use in the treatment of drug addiction and as antidiarrheals. The dosage of these compounds is dependent upon various factors, such as the particular compound employed and the particular response obtained. Typical dosages for use as an analgesic vary from 0.1 to 6.0 mg/kg per day administered parenterally.

The manufacture of the instant novel compounds is conveniently achieved by processes adapted to the synthesis of peptides, i.e., both solution synthesis and solid-phase peptide syntheses. In the case of solution syntheses, the order in which the amino acids are coupled is not critical. Thus, the pentapeptide may be produced by coupling any two suitable units containing the desired amino acids.

A convenient method for preparing certain of the compounds of this invention involves the coupling of the C-terminal dipeptide optionally substituted with protecting groups, of the formula

H-W-Y-OH            (II)

wherein W and Y are as defined hereinbefore, with the N-protected tripeptide active ester of the formula

□—Tyr-Gly-Gly-OX         (III)

wherein □ represents an N-protecting group and X represents an ester group to give the N-blocked pentapeptide of the formula

□—Tyr-Gly-Gly-W-Y-OH         (IV)

wherein □, W and Y are as hereinbefore defined. This N-blocked pentapeptide of formula (IV) is then deprotected in a conventional manner to give the desired pentapeptide.

Suitable solvents for use in these coupling reactions include, but are not limited to, methylene chloride, tetrahydrofuran and dimethylformamdide. The use of N-methyl-morpholine facilitates the reaction.

Alternatively, the desired peptide can be obtained by solid-phase peptide synthesis which consists of first attaching to a polymer support, e.g., a chloromethylated copolymer, styrene-1% divinylbenzene, the optionally N-protected C-terminal amino acid, followed by removal of the N-protecting group, and coupling, in the presence of a suitable dehydrating agent, e.g., dicyclohexylcarbodiimide, successively with each of the appropriate N-protected (if necessary) amino acids.

Suitable active esters for use in this invention are those which cause the acid function of the amino acid to become more reactive such as alkyl esters with electron withdrawing (negative) substituents, vinyl esters, enol esters, phenyl esters, thiophenyl esters, nitrophenyl esters, 2,4-dinitrophenyl esters, trichlorophenyl esters, pentachlorophenyl ester, and nitrophenylthiol esters. The use of pentachlorophenyl esters and 2,4,5-trichlorophenyl esters are particularly preferred for the preparation of the present invention.

The amino functions of the intermediates of this invention may be protected by commonly used amino protecting groups such as aryl-lower alkyl groups, such as diphenylmethyl or triphenylmethyl groups, which are optionally substituted by halogen, nitro, lower alkyl or lower alkoxy, for example; benzhydryl, trityl, and di-paramethoxybenzhydryl; acyl groups, such as formyl, trifluoroacetyl, phthaloyl, p-toluenesulphonyl, benzenesulphonyl, benzenesulphenyl and o-nitrophenylsulphenyl; groups derived from carbonic acid or thiocarbonic acid, such as carbobenzoxy groups which are optionally substituted in the aromatic radical by halogen atoms, nitro groups or lower alkyl, lower alkoxy or lower carbalkoxy groups, for example, carbobenzoxy, p-bromocarbobenzoxy or p-chlorocarbobenzoxy, p-nitrocarbobenzoxy and p-methoxycarbobenzoxy; coloured benzyloxycarbonyl groups such as p-phenylazobenzyloxycarbonyl and p-(p'-methoxyphenylazo)benzyloxycarbonyl, tolyloxycarbonyl, 2-phenyl-2-propoxycarbonyl, 2-tolyl-2-propoxycarbonyl and 2-(parabiphenylyl)-2-propoxycarbonyl; and aliphatic oxycarbonyl groups, such as t-butoxycarbonyl, allyloxycarbonyl, cyclopentyloxycarbonyl, t-amyloxycarbonyl. A particularly preferred N-protecting group for use in this invention is the t-butoxycarbonyl group.

The amino groups can also be protected by forming enamines, obtained by reaction of the amino group with 1,3-diketones, for example benzoylacetone, or acetylacetone.

Protecting groups are conveniently removed by reactions such as reduction with sodium in liquid ammonia, hydrogenolysis (for instance, in the presence of a palladium black catalyst), treatment with a hydrohalo acid (such as hydrobromic, hydrofluoric or hydrochloric acids) in acetic acid, or treatment with trifluoroacetic acid.

The following examples describe in detail the preparation of compounds illustrative of the present invention. It will be apparent to those skilled in the art that many modifications, both of materials and methods, may be practiced without departing from the purpose and intent of this disclosure. Throughout the examples hereinafter set forth, temperatures are given in degrees Centigrade (° C.) and relative amounts in parts by weight, except as otherwise noted.

EXAMPLE 1

A solution of 19.5 parts N-t-butoxycarbonylglycine 2,4,5-trichlorophenyl ester and 8.3 parts glycine benzyl ester in 200 parts methylene chloride is stirred overnight at room temperature. The solvent is then removed by evaporation under reduced pressure. The crude dipeptide is then subjected to low pressure column chromatography on silica gel to afford N-t-butoxycarbonylglcylglycine benzyl ester.

EXAMPLE 2

10.3 Parts N-t-butoxycarbonylglycylglycine benzyl ester is dissolved in 200 parts dioxane and treated with a 10 fold excess of 2 N hydrochloric acid in dioxane for 10 minutes. Removal of the solvent under reduced pressure affords pure glycylglycine benzyl ester hydrochloride.

EXAMPLE 3

A solution of 4.4 parts glycylglycine benzyl ester hydrochloride, 9.1 parts N-t-butoxycarbonyl-L-tyrosine 2,3,5-trichlorophenyl ester and 1.8 parts N-methylmorpholine in 150 parts methylene chloride is stirred overnight at room temperature. The solvent is then removed by evaporation under reduced pressure. The crude material is subjected to low-pressure column chromatography on silica gel to afford N-t-butoxycarbonyl-L-tyrosylglycylglycine benzyl ester.

EXAMPLE 4

To a solution of 2.8 parts N-t-butoxycarbonyl-L-tyrosylglycylclycine benzyl ester in 160 parts methanol is added 0.4 part palladium black metal catalyst. The resulting mixture is shaken with hydrogen at room temperature at atmospheric pressure for about 5 hours. The catalyst is then removed by filtration, and the solvent removed by evaporation at reduced pressure. The resulting crude material is purified using low pressure chromatography to afford N-t-butoxycarbonyl-L-tyrosylglycylglycine.

EXAMPLE 5

A solution of 26.6 parts N-t-butoxycarbonyl-L-tryptophan 2,4,5-trichlorophenyl ester and 12.0 parts L-methionine benzyl ester in 200 parts methylene chloride is stirred overnight at room temperature. The solvent is then removed by evaporation under reduced pressure. The crude dipeptide is then subjected to low-pressure column chromatography on silica gel to afford N-t-butoxycarbonyl-L-tryptophyl-L-methionine benzyl ester.

EXAMPLE 6

17.1 Parts N-t-butoxycarbonyl-L-tryptophyl-L-methionine benzyl ester is dissolved in 200 parts dioxane and treated with a 10 fold excess of 2N hydrochloric acid in dioxane for 10 minutes. Removal of the solvent under reduced pressure affords pure L-tryptophyl-L-methionine benzyl ester hydrochloride.

EXAMPLE 7

10.0 Parts N-t-butoxycarbonyl-L-tyrosylglycylglycine and 2.4 parts N-methylmorpholine are dissolved in 125 parts dimethylformamide and cooled to −15° C. Then 3.8 parts isobutyl chloroformate is added dropwise over a 30 minute period while maintaining the temperature at −15° C. Then, a solution of 12.7 parts L-tryptophyl-L-methionine benzyl ester hydrochloride in 50 parts dimethylformamide is slowly added at −15° C. and the mixture is stirred at this temperature for 30 minutes. The cooling apparatus is removed and the mixture is stirred at ambient temperature for an additional 2 hours. The product is isolated by diluting the reaction mixture with 10 volumes water and extracting with ethyl acetate. The ethyl acetate extracts are combined, dried over anhydrous sodium sulfate and stripped to dryness under reduced pressure. Purification of the residue by low pressure column chromatography affords N-t-butoxycarbonyl-L-tyrosylglycylglycyl-L-tryptophyl-L-methionine benzyl ester.

EXAMPLE 8

21.1 Parts N-t-butoxycarbonyl-L-tyrosylglycylglycyl-L-tryptophyl-L-methionine benzyl ester is dissolved in 70 parts methanol and the solution cooled to 10° C. Then, 90 parts by volume of 1 N sodium hydroxide solution is added dropwise with stirring while maintaining the temperature below 20° C. After standing at room temperature for 1 hour, the methanol is removed by evaporation under reduced pressure. The solution is washed once with ethyl ether to remove benzyl alcohol and the aqueous layer acidified with 90 parts by volume 1 N hydrochloric acid. The solid which results is filtered and washed with water to afford N-t-butoxycarbonyl-L-tyrosylglycylglycyl-L-tryptophyl-L-methionine.

The N-t-butoxycarbonyl-L-tyrosylglycylglycyl-L-tryptophyl-L-methionine is dissolved in 100 parts dioxane and stirred with a ten-fold excess of 2 N hydrochloric acid at room temperature for 15 minutes. The solvent is then removed under reduced pressure and the residue is triturated with ethyl ether. The resulting solid is precipitated from the mixture of methanol and ether to afford L-tyrosylglycylglycyl-L-tryptophyl-L-methionine hydrochloride. This compound is represented by the following formula H-Tyr-Gly-Gly-Trp-Met-OH . HCl

EXAMPLE 9

The hydrochloride acid addition salt may be converted into other suitable salts, or to the free base, by standard procedures, such as ion exchange methods.

17.3 Parts L-tyrosylglycylglycyl-L-tryptophyl-L-methionine hydrochloride is dissolved in 250 parts by volume of 20% acetic acid and passed slowly through an IR-45 ion exchange column in the acetate form. The column is washed with 20% acetic acid until no more peptide is eluted. Fractions containing the product are combined and the solvent removed by stripping under reduced pressure at room temperature. The residual glass is dissolved in 75 parts water and lyophilized to give L-tyrosylglycylglycyl-L-tryptophyl-L-methionine acetic acid salt. This compound is represented by the following formula H-Tyr-Gly-Gly-Trp-Met-OH . acetic acid When water is substituted for the 20% acetic acid above, and a hydroxide ion exchange column is used, the above procedure gives the free base, which is represented by the following formula H-Tyr-Gly-Gly-Trp-Met-OH

EXAMPLE 10

When an equivalent quantity of N-t-butoxycarbonyl-L-tyrosine 2,4,5-trichlorophenyl ester is substituted for the N-t-butoxycarbonyl-L-tryptophan 2,4,5-trichlorophenyl ester of Example 5 and the procedure detailed therein substantially repeated, there is obtained N-t-butoxycarbonyl-L-tyrosyl-L-methionine benzyl ester.

Treatment of the above dipeptide with 2 N hydrochloric acid as set out in Example 6 affords L-tyrosyl-L-methionine benzyl ester hydrochloride.

EXAMPLE 11

When an equivalent quantity of L-tyrosyl-L-methionine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycyl-L-tyrosyl-L-methionine benzyl ester. Repetition of the procedure detailed in Example 8 using an equivalent quantity of N-t-butoxycarbonyl-L-tyrosyl-glycylglycyl-L-tyrosyl-L-methionine benzyl ester affords L-tyrosylglycylglycyl-L-tyrosyl-L-methionine hydrochloride. This compound is represented by the following formula H-Tyr-Gly-Gly-Tyr-Met-OH.HCl

EXAMPLE 12

When an equivalent quantity of N-t-butoxycarbonyl-p-t-butyl-L-phenylalanine pentachlorophenyl ester is substituted for the N-t-butoxycarbonyl-L-tryptophan 2,4,5-trichlorophenyl ester of Example 5 and the procedure detailed therein substantially repeated, there is obtained N-t-butoxycarbonyl-p-t-butyl-L-phenylalanyl-L-methionine benzyl ester.

Treatment of the above dipeptide with 2 N hydrochloric acid as set out in Example 6 affords p-t-butyl-L-phenylalanyl-L-methionine benzyl ester hydrochloride.

EXAMPLE 13

When an equivalent quantity of p-t-butyl-L-phenylalanyl-L-methionine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycyl-p-t-butyl-phenylalanyl-L-methionine benzyl ester.

Repetition of the procedure detailed in Example 8 using an equivalent quantity of N-t-butoxycarbonyl-L-tyrosylglycylglycyl-p-t-butyl-L-phenylalanyl-L-methionine benzyl ester affords L-tyrosylglycylglycyl-p-t-butyl-L-phenylalanyl-L-methionine hydrochloride. This compound is represented by the following formula

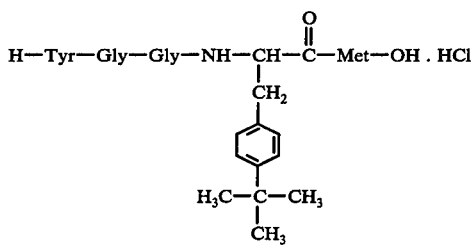

EXAMPLE 14

When an equivalent quantity of N-t-butoxycarbonyl-hexahydro-L-phenylalanine pentachlorophenyl ester is substituted for the N-t-butoxycarbonyl-L-tryptophan 2,4,5-trichlorophenyl ester of Example 5 and the procedure detailed therein substantially repeated, there is obtained N-t-butoxycarbonylhexahydro-L-phenylalanyl-L-methionine benzyl ester.

Treatment of the above dipeptide with 2 N hydrochloric acid as set out in Example 6 affords hexahydro-L-phenylalanyl-L-methionine benzyl ester hydrochloride.

EXAMPLE 15

When an equivalent quantity of hexahydro-L-phenylalanyl-L-methionine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycylhexahydro-L-phenylalanyl-L-methionine benzyl ester.

Repetition of the procedure detailed in Example 8 using an equivalent quantity of N-t-butoxycarbonyl-L-tyrosylglycylglycylhexahydro-L-phenylalanyl-L-methionine benzyl ester affords L-tyrosylglycylglycylhexahydro-L-phenylalanyl-L-methionine hydrochloride.

This compound is represented by the following formula

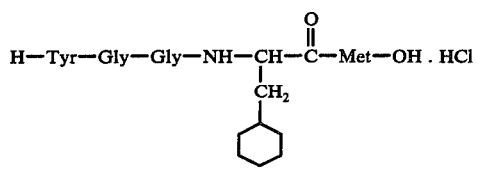

EXAMPLE 16

When an equivalent quantity of N-t-butoxycarbonyl-β-(2-thienyl)-L-alanine 2,4,5-trichlorophenyl ester is substituted for the N-t-butoxycarbonyl-L-tryptophan 2,4,5-trichlorophenyl ester of Example 5 and the procedure detailed therein substantially repeated, there is obtained N-t-butoxycarbonyl-β-(2-thienyl)-L-alanyl-L-methionine benzyl ester.

Treatment of the above dipeptide with 2 N hydrochloric acid as set out in Example 6 affords β-(2-thienyl)-L-alanyl-L-methionine benzyl ester hydrochloride.

EXAMPLE 17

When an equivalent quantity of β-(2-thienyl)-L-alanyl-L-methionine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycyl β-(2-thienyl)-L-alanyl-L-methionine benzyl ester.

Repetition of the procedure detailed in Example 8 using an equivalent quantity of N-t-butoxycarbonyl-L-tyrosylclycylglycyl-β-(2-thienyl)-L-alanyl-L-methionine benzyl ester affords L-tyrosylglycylglycyl-β-(2-thienyl)-L-alanyl-L-methionine hydrochloride. This compound is represented by the following formula

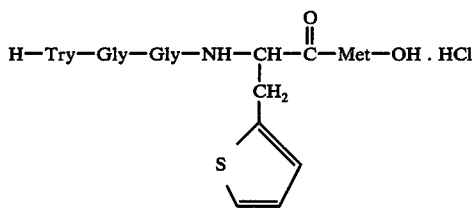

EXAMPLE 18

A solution of 19.5 parts N-t-butoxycarbonylglycine 2,4,5-trichlorophenyl ester and 11.1 parts L-leucine benzyl ester in 200 parts methylene chloride is stirred overnight at room temperature. The solvent is then removed by evaporation under reduced pressure. The crude dipeptide is then subjected to low-pressure column chromatography on silica gel to afford N-t-butoxycarbonylglycyl-L-leucine benzyl ester.

Treatment of the above dipeptide with 2 N hydrochloric acid as set out in Example 6 affords glycyl-L-leucine benzyl ester hydrochloride.

EXAMPLE 19

When an equivalent quantity of glycyl-L-leucine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycylglycyl-L-leucine benzyl ester.

Repetition of the procedure detailed in Example 8 using an equivalent quantity of N-t-butoxycarbonyl-L-tyrosylglycylglycylglycyl-L-leucine benzyl ester affords L-tyrosylglycylglycylglycyl-L-leucine hydrochloride. This compound is represented by the following formula H-Tyr-Gly-Gly-Gly-Leu-OH.HCl

EXAMPLE 20

When an equivalent quantity of N-t-butoxycarbonylD-tyrosine 2,4,5-trichlorophenyl ester is substituted for the N-t-butoxycarbonyl-L-tryptophan 2,4,5-trichlorophenyl ester of Example 5 and the procedure detailed therein substantially repeated, there is obtained N-t-butoxycarbonylD-tyrosyl-L-methionine benzyl ester.

Treatment of the above dipeptide with 2 N hydrochloric acid as set out in Example 6 affords D-tyrosyl-L-methionine benzyl ester hydrochloride.

EXAMPLE 21

When an equivalent quantity of D-tyrosyl-L-methionine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycyl-D-tyrosyl-L-methionine benzyl ester.

Repetition of the procedure detailed in Example 8 using an equivalent quantity of N-t-butoxycarbonyl-L-tyrosylglycylglycyl-D-tyrosyl-L-methionine benzyl ester affords L-tyrosylglycylglycyl-D-tyrosyl-L-methionine hydrochloride. This compound is represented by the following formula H-Tyr-Gly-Gly-Tyr-Met-OH.HCl(L,D,L)

What we claim is:
1. A compound of the formula

H-Tyr-Gly-Gly-W-Y-OH wherein Y is Leu or Met; W is β-thienyl-Ala; and the stereochemical configuration of each of the optically active amino acid residues may independently be D, L, or DL.

2. The compound according to claim 1 which is L-tyrosylglycylglycyl-β-thienyl-L-alanyl-L-leucine.

3. The compound according to claim 1 which is L-tyrosylglycylglycyl-β-thienyl-L-alanyl-L-methionine.

* * * * *